(12) United States Patent
Boswell et al.

(10) Patent No.: US 6,680,383 B1
(45) Date of Patent: Jan. 20, 2004

(54) METHOD FOR MAKING NEVIRAPINE

(75) Inventors: Robert Frederick Boswell, Richmond, VA (US); Bernard Franklin Gupton, Midlothian, VA (US); Young Sek Lo, Chester, VA (US)

(73) Assignee: Boehringer Ingelheim Chemicals, Inc., Petersburg, VA (US)

( * ) Notice: Subject to any disclaimer, the term of this patent is extended or adjusted under 35 U.S.C. 154(b) by 0 days.

(21) Appl. No.: 10/454,991

(22) Filed: Jun. 5, 2003

Related U.S. Application Data

(60) Provisional application No. 60/392,690, filed on Jun. 28, 2002.

(51) Int. Cl.⁷ .................... C07D 471/14; C07D 213/44; C07D 211/72
(52) U.S. Cl. .................... 540/495; 546/262; 546/310
(58) Field of Search .................... 540/495; 546/310, 546/262

(56) References Cited

U.S. PATENT DOCUMENTS

| | | | |
|---|---|---|---|
| 5,366,972 A | 11/1994 | Hargrave et al. | 514/220 |
| 5,569,760 A | 10/1996 | Schneider et al. | 540/495 |

*Primary Examiner*—Bruck Kifle
(74) *Attorney, Agent, or Firm*—Robert P. Raymond; Alan R. Stempel; Mary-Ellen M. Devlin

(57) ABSTRACT

A process for making nevirapine, comprising the following steps:

(a) reacting a 2-halo-3-pyridinecarbonitrile of the formula

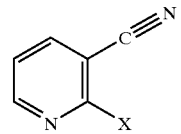

wherein X is a fluorine, chlorine, bromine or iodine atom, preferably chlorine or bromine, with cyclopropylamine, to yield 2-(cyclopropylamino)-3-pyridinecarbonitrile;

(b) hydrolyzing the 2-(cyclopropylamino)-3-pyridinecarbonitrile to yield 2-(cyclopropylamino)-3-pyridine carboxylic acid;

(c) isolating the 2-(cyclopropylamino)-3-pyridine carboxylic acid from the reaction medium;

(e) treating the 2-(cyclopropylamino)-3-pyridine carboxylic acid with a chlorinating agent, to yield 2-(cyclopropylamino)-3-pyridinecarbonyl chloride;

(f) reacting the 2-(cyclopropylamino)-3-pyridine carbonyl chloride with a 2-halo-4-methyl-3-pyridinamine of the formula

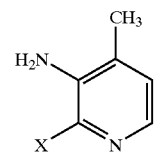

wherein X is a fluorine, chlorine, bromine or iodine atom, preferably chlorine or bromine, to produce an N-(2-halo-4-methyl-3-pyridinyl)-2-(cyclo-propylamino)-3-pyridinecarboxamide; and (g) cyclizing the N-(2-halo-4-methyl-3-pyridinyl)-2-(cyclopropylamino)-3-pyridinecarboxamide by treatment with a strong base, to yield nevirapine.

6 Claims, No Drawings

METHOD FOR MAKING NEVIRAPINE

CROSS-REFERENCE TO RELATED APPLICATIONS

Benefit of U.S. provisional application serial No. 60/392,690, filed on Jun. 28, 2002, is hereby claimed.

BACKGROUND OF THE INVENTION

1. Technical Field

The invention relates to an improved method for making nevirapine, and to several novel intermediates which are produced during the course of carrying out the improved method.

2. Background Information

Nevirapine is a non-nucleoside inhibitor of HIV reverse transcriptase, which is useful in the treatment of HIV infection in humans. The chemical name for nevirapine is 11-cyclopropyl-5,11-dihydro-4-methyl-6H-dipyrido [3,2-b:2', 3'-e][1,4]diazepin-6-one. Its structural formula is:

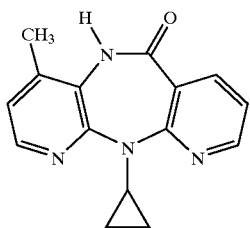

The earliest known synthesis of nevirapine, by Hargrave et al., is described in U.S. Pat. No. 5,366,972. The synthetic method employed is depicted in the following reaction Scheme 1.

In the method of Hargrave et al., 2-chloronicotinoyl chloride is formed by reacting 2-chloronicotinic acid with thionyl chloride. Next, as shown in Scheme 1, the reaction of 2-chloronicotinoyl chloride with 2-chloro-4-methyl-3-pyridinamine produces 2-chloro-N-(2-chloro-4-methyl-3-pyridinyl)-3-pyridinecarboxamide. This is reacted with cyclopropylamine to give N-(2-chloro-4-methyl-3-pyridinyl)-2-(cyclopropylamino)-3-pyridinecarboxamide. The final step is the cyclization to produce nevirapine, which occurs on treatment of the final intermediate with sodium hydride.

A refinement of the above process, described by Schneider et al. in U.S. Pat. No. 5,569,760, is presently used for the commercial manufacture of nevirapine. In this improvement of the synthesis, the reaction of 2-chloro-N-(2-chloro-4-methyl-3-pyridinyl)-3-pyridinecarboxamide with cyclopropylamine is carried out in the presence of a neutralizing agent, which is an oxide or hydroxide of an an element of the second main or second subgroup of the periodic table. It is preferred to use as the neutralizing agent an oxide or hydroxide of an alkaline earth metal or of zinc, with calcium oxide being particularly preferred.

While the synthesis provided by U.S. Pat No. 5,366,972 is the best known to date, it nevertheless suffers from several significant drawbacks. First, because the reaction of cyclopropylamine with 2-chloro-N-(2-chloro-4-methyl-3-pyridinyl)-3-pyridinecarboxamide is carried out at elevated temperature (between 130° to 150° C.) and because cyclopropyl amine is so highly volatile, this reaction must be carried out in a high pressure reaction vessel. Second, 2-chloro-N-(2-chloro-4-methyl-3-pyridinyl)-3-pyridinecarboxamide becomes thermally unstable above about 145° C., and allowing the temperature of the reaction mixture to go above this temperature poses the risk of an explosion. Therefore, it is prudent to carefully control the temperature of the reaction mixture so that it remains below 145° C. until substantially all of this material has been consumed by the reaction. Maintaining such tight control of the temperature of the reaction mixture is difficult at best, and it is made all the more difficult by the fact that the Scheme 1

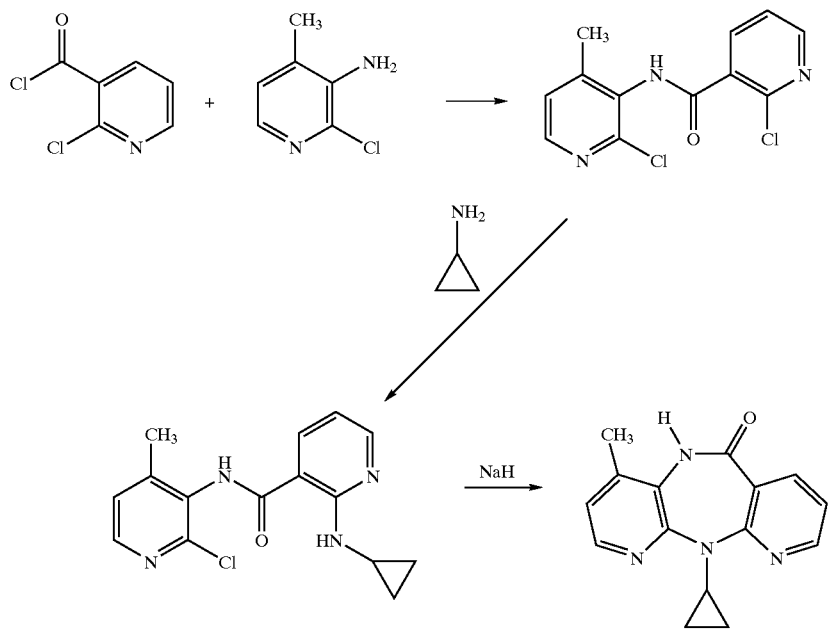

reaction is itself exothermic. Third, it is necessary to remove the neutralizing agent by filtration. Finally, due to the production of side products, the overall yield of the synthesis is only about 25%.

There is thus a need for a better synthesis for nevirapine.

BRIEF SUMMARY OF THE INVENTION

The present invention satisfies this need by providing a synthesis for nevirapine that is safer, higher yielding and more economical than any method yet known.

DETAILED DESCRIPTION OF THE INVENTION

The improved synthesis of nevirapine provided by the present invention is depicted below in reaction Scheme 2.

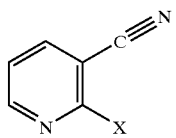

wherein X is a fluorine, chlorine, bromine or iodine atom, preferably chlorine or bromine, is reacted with cyclopropylamine (2), to yield 2-(cyclopropylamino)-3-pyridinecarbonitrile (3). This reaction is carried out in an inert, organic solvent, with or without water, at elevated temperature. Appropriate organic solvents are $C_1$ to $C_6$ straight or branched chain alcohols, tetrahydrofuran, dimethylformamide, diglyme, toluene, and the like. The preferred solvents are ethanol and 1-propanol, with or with-

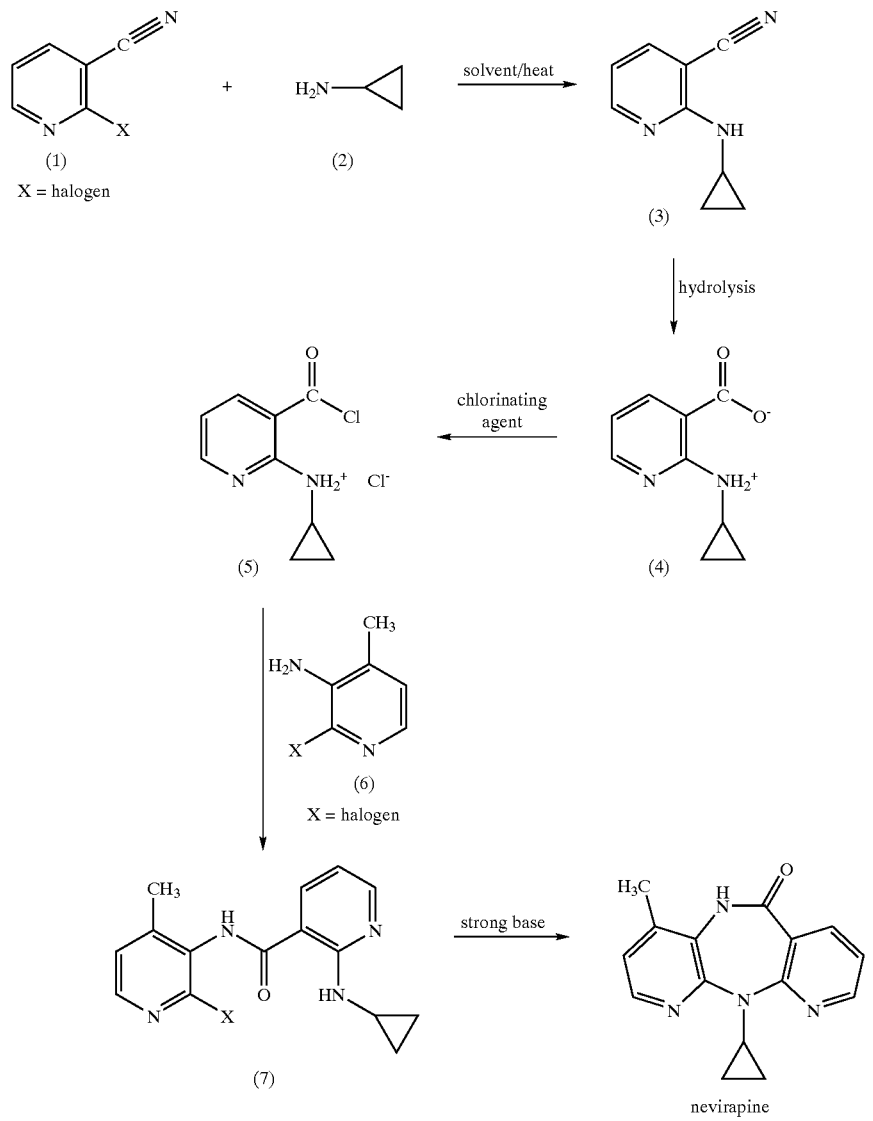

In the first reaction step, a 2-halo-3-pyridinecarbonitrile (1) of the formula out water. Optionally, a base, either organic or inorganic, such as triethylamine, diisopropylethylamine, potassium phosphate, sodium carbonate, potassium carbonate and the like, can be added as an acid scavenger. The reaction can be carried out at a temperature between ambient temperature and reflux temperature, but it is preferred that the temperature be between 77° and 100° C.

The 2-(cyclopropylamino)-3-pyridinecarbonitrile is next hydrolyzed to yield 2-(cyclopropylamino)-3-pyridine carboxylic acid (4), which predominantly exists as the zwitterion when isolated according to the disclosed procedures and is, therefore, represented as such in Scheme 2. Isolation of the nitrile prior to hydrolysis is optional. The hydrolysis of the nitrile to the carboxylic acid can be carried out in a conventional manner, using a strongly acidic or basic solution. The hydrolysis is preferably carried out using an aqueous mixture of hydrogen peroxide and a strong base, such as sodium or potassium hydroxide, or an aqueous mixture of a strong base, such as sodium or potassium hydroxide, and an alcohol of 1 to 6 carbon atoms. Most preferably, the hydrolysis is carried out using aqueous 1-propanol and potassium hydroxide. Heating to reflux will accelerate the rate of hydrolysis.

The 2-(cyclopropylamino)-3-pyridine carboxylic acid is next isolated from the reaction medium. This is conveniently accomplished by adjusting the pH to the isoelectric point, which is reached at about pH 6. This produces the zwitterion, which precipitates out and is then separated by filtration and dried. If an aqueous alcohol and a base are used to conduct the hydrolysis, the alcohol is first removed by distillation.

Subsequently, the 2-(cyclopropylamino)-3-pyridine carboxylic acid is treated with a chlorinating agent, to yield 2-(cyclopropylamino)-3-pyridinecarbonyl chloride (5). Appropriate chlorinating agents are, for example, thionyl chloride, phosphorus oxychloride, phosphorus trichloride, phosphorus pentachloride, phosgene, and oxalyl chloride. The chlorination is performed in a manner known to those skilled in the art of organic synthesis. In general it is preferred to reflux the carboxylic acid (4) with the chlorinating agent, which will either be used neat or in solution with a suitable aprotic solvent such as, for example, toluene, acetonitrile, tetrahydrofuran, or the like. It is preferred to perform the chlorination by refluxing with neat thionyl chloride, any excess of which can later be conveniently removed by evaporation. As most chlorinating agents produce hydrochloric acid, the product (5) of this reaction step is depicted in Scheme 2 as the hydrochloride.

The 2-(cyclopropylamino)-3-pyridinecarbonyl chloride (5) is next reacted with a 2-halo-4-methyl-3-pyridinamine (6) of the formula

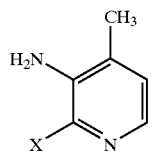

wherein X is a fluorine, chlorine, bromine or iodine atom, preferably chlorine or bromine. The most preferred reactant is 2-chloro-4-methyl-3-pyridinamind,. This produces an N-(2-halo-4-methyl-3-pyridinyl)-2-(cyclopropylamino)-3-pyridinecarboxamide(7), wherein X is a fluorine, chlorine, bromine or iodine atom, preferably chlorine or bromine. It is essential to first remove any remaining chlorinating agent, as this would react with the pyridineamine. If a highly volatile chlorinating agent, such as thionyl chloride, is used neat, then it may be removed by evaporation to leave the acid chloride (5) as a solid. If the chlorination is done in a solvent, then it is preferable to employ a solvent that is high boiling, so that chlorinating agent may be removed by evaporation, leaving the acid chloride dissolved in the solvent. In any event, the acid chloride (5) is to be maintained under anhydrous conditions. The acid chloride (5) and the pyridineamine (6) are reacted by dissolution in a suitable anhydrous solvent such as, for example acetonitrile, tetrahydrofuran, diglyme, dimethylformamide, dioxane, methylene chloride, or toluene. Optionally a base, either organic or inorganic, such as triethylamine, diisopropylethylamine, potassium phosphate, potassium hydrogen phosphate, sodium carbonate, sodium hydroxide, potassium hydroxide or the like, may be added to the reaction mixture as an acid scavenger. The reaction rate may be increased by heating up to the boiling point of the solvent.

Finally, the carboxamide (7) is cyclized to yield nevirapine. The cyclization is induced by treating the carboxamide (7) with a strong base, such as sodium hydride (NaH) r sodium bexamethyldisilazane (NaHMDS) in an inert anhydrous organic solvent, such as diglyme, toluene, or tetrahydrofuran, at from −30° C. to 130° C.

The synthesis of the intermediate 2-(cyclopropylamino)-3-pyridinecarbonitrile by means of the reaction of 2-chloro-3-pyridinecarbonitrile with cyclopropylamine is known from G. E. Hardtmann et al, *J. Med. Chem.* 1974, 17, 636.

The intermediates, 2-(cyclopropylamino)-3-pyridine carboxylic acid (4) and 2-(cyclopropylamino)-3-pyridinecarbonyl chloride (5) are believed to be novel and, thus, are considered to be aspects of the invention.

It is preferred to use 2-chloro-3-pyridinecarbonitrile as starting material (1) since syntheses for this substance are known and it is commercially available. Other 2-halo-3-pyridinecarbonitriles can be readily synthesized in an analogous manner.

Cyclopropylamine, the starting material (2), is also commercially available.

It is preferred to use 2-chloro-4-methyl-3-pyridinamine as reactant (6) since syntheses for this substance are known from U.S. Pat. Nos. 6,399,781; 5,686,618; 5,668,287; 5,654,429 and 5,200,522. Other 2-halo-4-methyl-3-pyridinamines can be readily synthesized in an analogous manner.

The following examples further illustrate the preparation of nevirapine using the improved process provided by the present invention. While each step of the reaction sequence can be carried out by first isolating the product of the preceding step, some of the reaction steps may be carried out sequentially, in one reaction vessel, without isolation of the intermediate formed by the preceding step, thus reducing costs associated with vessel time, cleanup, and labor. The following Examples 1–6 illustrate the approach wherein the intermediate formed at the completion of each step is isolated. Examples 7 and 8 illustrate how some of the reaction steps may be carried out sequentially, in one reaction vessel, without isolation of the intermediate formed by the preceding step.

EXAMPLE 1

Preparation of 2-(Cyclopropylamino)-3-pyridinecarbonitrile

A reaction flask equipped with a mechanical stirrer, temperature controller, condenser and addition funnel was charged with 2-chloro-3-pyridinecarbonitrile (69.25 g, 0.50 mol), 300 ml of ethanol and 200 ml of water. With agitation, cyclopropylamine ( 114g, 2.0 mol) was added dropwise over 30 minutes at a temperature<30° C. When the addition was completed, the stirred reaction mixture was heated to reflux temperature for 20 hours. The reaction mixture was cooled to 60° C. and then 350 ml of excess cyclopropylamine and ethanol were removed by vacuum distillation using water aspirator vacuum. The remaining aqueous solution was cooled to ambient temperature and allowed to stand overnight. The solid product was collected by filtration and the filter cake rinsed with water. The yield was 81.51 g (theoretical yield is 79.5 g).

EXAMPLE 2

Preparation of 2-(Cyclopropylamino)-3-pyridine Carboxylic Acid (Zwitterion)

A 45% aqueous KOH solution (187g, 1.5 mol) was charged to a mixture of the product from Example 1 and 300 ml of 1-propanol. The mixture was heated at reflux temperature for about 5 hours whereupon TLC analysis showed complete hydrolysis of the nitrile. The reaction mixture was cooled to ambient temperature and treated with 94 g of water that was needed to remove the 1-propanol by azeotropic distillation. About 330 g of water/1-propanol azeotrope was distilled off at 62° C. and 21.1 in. Hg. Water (130 g) was added to the reaction mixture and the mixture chilled to 5–10° C. Concentrated hydrochloric acid (148 g, 1.5 mol) was added at such a rate that the temperature could be maintained below 30° C. After about 80–90% of the acid was added the zwitterion began to precipitate out, making the mixture quite thick. When all the acid had been added, the solid product was collected by filtration, using 90 ml of cold water to rinse out the reaction vessel onto the filter cake. The product was dried to yield 68.12 g. of the zwitterion.

EXAMPLE 3

Preparation of 2-(Cyclopropylamino)-3-pyridinecarbonyl Chloride

Thionyl chloride (25 ml, 40.8 g, 0.343 mol) was charged in a thin stream to 9.00 g, 0.048 mol, of 2-(cyclopropylamino)-3-pyridine carboxylic acid from Example 2 in acetonitrile. The mixture was heated at reflux temperature for 30 minutes. The mixture was allowed to cool and the thionyl chloride was distilled off at 40° C./23 in. Hg until the pot contents became thick. Toluene (25 ml) was added and distillation of thionyl chloride and toluene at 40° C. was continued until about one-half of the liquid was distilled. The remaining solution was allowed to cool and stirred to promote crystallization. Heptane (25 ml) was added to the mixture with stirring and the mixture filtered under a nitrogen atmosphere to obtain the title compound.

EXAMPLE 4

Preparation of N-(2-Chloro-4-methyl-3-pyridinyl)-2-(cyclopropylamino)-3-pyridinecarboxamide A solution of 2-chloro-4-methyl-3-pyridinamine (5.70 g, 0.040 mol) in 10 ml of acetonitrile was charged rapidly dropwise to a mixture of the acid chloride from Example 3, ground anhydrous potassium phosphate (8.49 g, 0.04 mol) and 40 ml of acetonitrile. The reaction mixture was heated at 50° C. for 20 hours and the reaction progress monitored by HPLC analysis. When the reaction was complete, the reaction mixture was cooled to ambient temperature and treated with 50 ml of water, giving a solution having a pH of about 4.5–5.

The mixture was acidified to pH 1 by addition of dilute HCl solution and stirred for 30 min at ambient temperature. The reaction mixture was filtered to remove any insoluble material and the filtrate was basified to pH 9–10 with dilute sodium hydroxide solution and stirred for 30 minutes at ambient temperature. The mixture was then acidified to pH 7–8 by addition of dilute HCl, forming a dark oily layer on top of the solution. Water was added, as this had been observed during past experiments of a similar nature to hasten crystallization. The oily layer crystallized slowly on stirring overnight. The solid product was collected and dried in a vacuum oven at 50° C. to obtain 9.37 g of the title compound.

EXAMPLE 5

Preparation of 11-Cyclopropyl-5,11-dihydro4-methyl-6H-dipyrido [3,2-b:2', 3'-e][4]diazepin-6-one (nevirapine) using Sodium Hexamethyldisilazane A reaction flask equipped with a magnetic stirrer, temperature controller thermodouple, addition funnel and condenser with an oil bubbler for exclusion of ambient air was inerted with nitrogen and charged with 3.02 g (0.010 mol) of N-(2-chloro-4-methyl-3-pyridinyl)-2-(cyclopropylamino)-3-pyridinecarboxamide from Example 4 and 30 ml of anhydrous THF. A 40% solution of sodium hexamethyldisilazane in THF (12.7 ml, 0.025 mol) was added dropwise maintaining the temperature of the reaction mixture at no more than 30° C. When the addition of the NaHMDS solution was completed, the reaction mixture was heated to reflux temperature (about 63–66° C.). When the reaction was completed (HPLC analysis), the mixture was cooled to ambient temperature. The reaction mixture was treated with 1.55 g (0.050 mol) of methanol and 0.45 g of water (0.025 mol). The mixture was concentrated on a rotary evaporator at 25–30 in. Hg with a 50–60° water bath temperature. The residual product weighing 4.44 g was triturated with 50 ml of water and the pH 10–12 solution was acidified to pH 3 by adding 10% HCl solution. The solid product was collected by filtration and the filter cake rinsed three times with 10 ml portions of water. The filter cake was dried in a vacuum oven at 50–60° C. to obtain nevirapine.

EXAMPLE 6

Preparation of 11-Cyclopropyl-5,11-dihydro4-methyl-6H-dipyridol [3,2-b:2', 3'-e][1,4]diazepin-6-one (nevirapine) using Sodium Hydride A 500 ml 4NRB flask with stirrer, temperature controller thermocouple, addition funnel and condenser with an oil bubbler to exclude air was inserted with nitrogen and charged with 15.00 g of 60% sodium hydride in a mineral oil slurry and 120 ml of diglyme. The mixture was heated to 130° C. and treated dropwise with a solution of 41.7 g (0.138 mol) of N-(2-chloro-4-methyl-3-pyridinyl)-2-(cyclopropylamino)-3-pyridinecarboxamide, from example 4, in 70 ml of diglyme at 80 ° C. The reaction mixture was heated at 130° C. until hydrogen evolution ceased. The mixture was cooled to ambient temperature and water (6.75 g) was added dropwise cautiously. When hydrogen evolution ceased, an additional 100 ml of water was added. Acetic acid (20 ml) was added to reduce the pH of the mixture from 11–13 to about 7. An additional 100 ml of water was added and the reaction mixture stirred under ambient conditions for 30 minutes while the product crystallized. The solid product was collected by filtration and the filter cake rinsed with 100 ml of water followed by 50 ml of cyclohexane to remove any residual mineral oil from the mineral oil-sodium hydride slurry. The wet cake was dried in a vacuum oven at 50° C. for 18 hours to obtain 35.58 g of nevirapine.

EXAMPLE 7

A One-Pot Synthesis of 2-(Cyclopropylamino)-3-pyridine Carboxylic Acid from 2-chloro-3-pyridinecarbonitrile

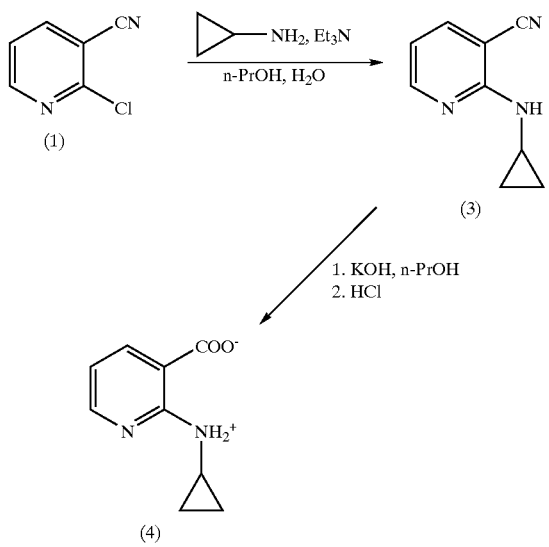

A one liter 4NRB flask with stirrer, condenser, temperature controller thermocouple and addition funnel was charged with 2-chloro-3-pyridinecarbonitrile. (27.70 g, 0.20 mol) followed by 120 ml of 1-propanol and 80 ml of water. Triethylamine (20.2 g, 0.20 mol) was added in one portion followed by addition of cyclopropylamine (17. 10 g, 0.30 mol) over a period of 2 minutes. The reaction mixture was heated at reflux (86–87° C.) and after 2.5 hours, a tlc analysis (silica gel, MTBE mobile phase) showed some product formation. After stirring at reflux for 16 hours, tlc analysis showed a little starting material remaining. HPLC analysis showed 22% starting material-75% 2-(cyclopropylamino)-3-pyridinecarbonitrile. An additional 0.1 mol (10.1 g) of triethylamine (total of 30.3 g, 0.30 mol of triethylamine) and 0.03 mol of cyclopropylamine (1.70 g) were added and the mixture continued to be heated at reflux for another 3 hours. HPLC analysis showed 15% starting material remaining. An additional 4.0 g of cyclopropylamine (total 0.40 mol) was added and the mixture heated at reflux for another 18 hours. At the end of that time HPLC analysis showed 2.9% starting material.

Potassium hydroxide (33.6 g, 0.60 mol) was added and the mixture heated to about 40° C. under vacuum for about 15 minutes to remove any volatile amines. The mixture was then heated at reflux for 5 hours under atmospheric pressure to hydrolyze the nitrile to the carboxylic acid. Water (80 mol) was added and n-propanol was distilled off as an azeotrope 10 with water (azeotrope boiling point is 87.7° C., 28.3% water, 71.7% n-propanol). When the distilling head temperature increased to 92° C. the distillation was stopped and the reaction mixture allowed to cool.

The reaction mixture was chilled to about 10° C. with an ice-methanol bath and 50 ml (59.2 g) of 37% HCl solution was added dropwise, maintaining the reaction mixture at no more than 25° C. All of the HCl was added and after stirring about 2 minutes longer crystallization of the 2-(cyclopropylamino)-3-pyridine carboxylic acid began and the product set up to a cake. Water (100 ml) was added to break up the solid mass and make the mixture stirrable. After about 30 minutes, the solid was collected by filtration. Additional solid was obtained by concentrating the filtrate. After drying by air aspiration for about 2 hours, the wet-cake solid weighed 23.02 g. HPLC showed 97% 2-(cyclopropylamino)-3-pyridine carboxylic acid and two small unknown impurity peaks of 1.8% and 1.3% concentrations. The solid was dried in a vacuum oven at 50° C. for 65 hours to yield 18.19 g.

EXAMPLE 8

A One-Pot Synthesis of N-(2-Chloro-4-methyl-3-pyridinyl)-2-(cyclopropylamino)-3-pyridinecarboxamide from 2-chloro-4-methyl-3-pyridinamine and 2-(cyclopropylamino)-3-pyridine Carboxylic Acid (Zwitterion)

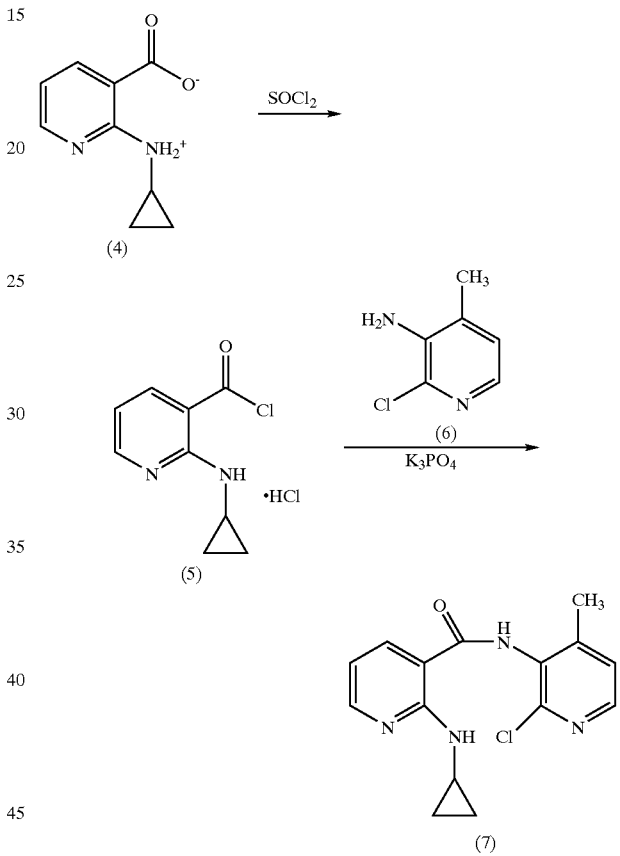

A 250 ml 4NRB flask equipped with a mechanical stirrer, condenser, addition funnel, and temperature controller thermocouple, was charged with 2-(cyclopropylamino)-3-pyridine carboxylic acid (18.46 g, 0.10 mol). Thionyl chloride (22 ml, 0.30 mol) was added in a thin stream to the reaction flask with stirring and the mixture heated to reflux for 32 minutes. The reaction mixture was cooled and the condenser was replaced with a vacuum distillation head. The thionyl chloride was distilled off at 40° C. at 23 in Hg vacuum until the distillation pot contents became thick. Toluene (30 ml) was added and distillation continued until about most of the liquid was distilled off. Another 30 ml of toluene was added and about one-half of the solvent was distilled off under vacuum. Acetonitrile (60 ml) was added to the residual mixture. A solution of 2-chloro-4-methyl-3-pyridinamine (11.4 g, 0.080 mol) in 40 ml of acetonitrile was added dropwise and the reaction mixture heated to 50° C. and stirred overnight. Finely crushed potassium phosphate was added after the 2-chloro-4-methyl-3-pyridinamine addition. After 16 hrs at 50° C. 100 ml of water was added to the stirred reaction mixture (pH 4–5). The reaction mixture was filtered to remove a small quantity of insoluble material. The filtrate (2 layers) was basified to pH 10–11 with 50% aqueous NaOH solution and then acidified back to pH 8. Most of the product was found in the toluene layer by HPLC analysis. The toluene layer was extracted with 300 ml dilute HCl solution (pH 1). The aqueous acid layer was basified to pH 8 using 10% aqueous NaOH resulting in the separation of an oily layer that crystallized slowly with trituration. After standing over 2 days, the solid product was collected and dried in vacuum at 50° C. to yield 21.40 g tan solid title compound.

What is claimed is:

1. A process for making nevirapine, comprising the following steps:

(a) reacting a 2-halo-3-pyridinecarbonitrile of the formula

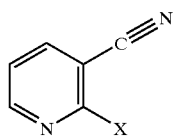

wherein X is a fluorine, chlorine, bromine or iodine atom, with cyclopropylamine, to yield 2-(cyclopropylamino)-3-pyridinecarbonitrile;

(b) hydrolyzing the 2-(cyclopropylamino)-3-pyridinecarbonitrile to yield 2-(cyclopropylamino)-3-pyridine carboxylic acid;

(c) isolating the 2-(cyclopropylamino)-3-pyridine carboxylic acid from the reaction medium;

(d) treating the 2-(cyclopropylamino)-3-pyridine carboxylic acid with a chlorinating agent, to yield 2-(cyclopropylamino)-3-pyridinecarbonyl chloride;

(e) reacting the 2-(cyclopropylamino)-3-pyridine carbonyl chloride with a 2-halo-4-methyl-3-pyridinamine of the formula

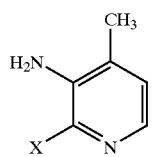

wherein X is a fluorine, chlorine, bromine or iodine atom, to produce an N-(2-halo4-methyl-3-pyridinyl)-2-(cyclopropylamino)-3-pyridinecarboxamide of the formula

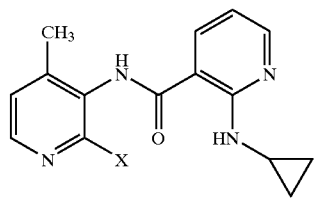

wherein X is a fluorine, chlorine, bromine or iodine atom, and (f) cyclizing the N-(2-halo-4-methyl-3-pyridinyl)-2-(cyclopropylamino)-3-pyridinecarboxamide by treatment with a strong base, to yield nevirapine.

2. 2-(Cyclopropylamino)-3-pyridine carboxylic acid.

3. 2-(Cyclopropylamino)-3-pyridinecarbonyl chloride.

4. A process for making 2-(cyclopropylamino)-3-pyridine carboxylic acid, which process comprises the following steps:

(a) reacting a 2-halo-3-pyridinecarbonitrile of the formula

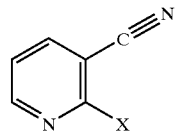

wherein X is a fluorine, chlorine, bromine or iodine atom, with cyclopropylamine, to yield 2-(cyclopropylamino)-3-pyridinecarbonitrile; and (b) hydrolyzing the 2-(cyclopropylamino)-3-pyridinecarbonitrile to yield 2-(cyclopropylamino)-3-pyridine carboxylic acid.

5. A process for preparing an N-(2-halo-4-methyl-3-pyridinyl)-2-(cyclopropylamino)-3-pyridinecarboxamide of the formula

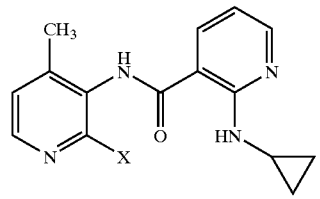

wherein X is a fluorine, chlorine, bromine or iodine atom, which comprises the following steps:

(a) treating 2-(cyclopropylamino)-3-pyridine carboxylic acid with a chlorinating agent, to yield 2-(cyclopropylamino)-3-pyridinecarbonyl chloride; and (b) reacting the 2-(cyclopropylamino)-3-pyridine carbonyl chloride with a 2-halo-4-methyl-3-pyridinamine of the formula

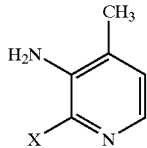

wherein X is a fluorine, chlorine, bromine or iodine atom, to produce the N-(2-halo-4-methyl-3-pyridinyl)-2-(cyclopropylamino)-3-pyridinecarboxamide.

6. A process for preparing an N-(2-halo-4-methyl-3-pyridinyl)-2-(cyclopropylamino)-3-pyridinecarboxamide which comprises reacting 2-(cyclopropylamino)-3-pyridine carbonyl chloride with a 2-halo-4-methyl-3-pyridinamine of the formula

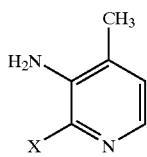

wherein X is a fluorine, chlorine, bromine or iodine atom.

* * * * *